United States Patent
Schroecker et al.

(10) Patent No.: US 9,655,592 B2
(45) Date of Patent: May 23, 2017

(54) METHOD AND APPARATUS FOR RENDERING AN ULTRASOUND IMAGE

(71) Applicant: General Electric Company, Schenectady, NY (US)

(72) Inventors: Gerald Schroecker, Salzburg (AT); Eduard Gröller, Vienna (AT); Alexey Karimov, Vienna (AT); Stefan Bruckner, Bergen (NO); Daniel Buckton, Salzburg (AT)

(73) Assignee: GENERAL ELECTRIC CORPORATION, Schenectady, NY (US)

( * ) Notice: Subject to any disclaimer, the term of this patent is extended or adjusted under 35 U.S.C. 154(b) by 67 days.

(21) Appl. No.: 14/549,768

(22) Filed: Nov. 21, 2014

(65) Prior Publication Data

US 2016/0143623 A1    May 26, 2016

(51) Int. Cl.
| | |
|---|---|
| G06K 9/00 | (2006.01) |
| A61B 8/08 | (2006.01) |
| A61B 8/14 | (2006.01) |
| G06T 11/00 | (2006.01) |
| G06T 15/08 | (2011.01) |

(52) U.S. Cl.
CPC .......... *A61B 8/5207* (2013.01); *A61B 8/0866* (2013.01); *A61B 8/14* (2013.01); *G06T 11/001* (2013.01); *G06T 15/08* (2013.01); *G06T 2200/08* (2013.01); *G06T 2207/10132* (2013.01); *G06T 2207/30044* (2013.01); *G06T 2207/30196* (2013.01); *G06T 2210/41* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,720,291 | A * | 2/1998 | Schwartz | A61B 8/06 128/916 |
| 6,102,861 | A * | 8/2000 | Avila | A61B 8/14 128/916 |
| 6,276,211 | B1 | 8/2001 | Smith | |
| 6,544,178 | B1 | 4/2003 | Grenon et al. | |
| 6,692,441 | B1 | 2/2004 | Poland et al. | |

(Continued)

FOREIGN PATENT DOCUMENTS

| | | |
|---|---|---|
| JP | 2014054378 A | 3/2014 |
| KR | 100656861 B1 | 12/2001 |

OTHER PUBLICATIONS

International Search Report from Corresponding PCT application PCT/US2015/061570 dated Mar. 15, 2016; 3 pages.

*Primary Examiner* — Anand Bhatnagar
(74) *Attorney, Agent, or Firm* — Grogan, Tuccillo & Vanderleeden, LLP

(57) ABSTRACT

A method for rendering an image from ultrasound image data includes dividing the ultrasound image data into at least a first group of voxels and a second group of voxels, based on comparing voxel echo intensity to a threshold value. The method further includes processing the first group of voxels according to a first protocol and processing the second group of voxels according to a second protocol. The method further includes generating an image that includes both the first group of processed voxels and the second group of processed voxels to enhance realism of the rendered image.

20 Claims, 4 Drawing Sheets

(56) References Cited

U.S. PATENT DOCUMENTS

| | | | |
|---|---|---|---|
| 7,399,278 B1 | 7/2008 | Ross | |
| 7,912,264 B2 * | 3/2011 | Freiburger | A61B 8/06 382/128 |
| 2004/0024302 A1 * | 2/2004 | Chalana | A61B 8/0858 600/407 |
| 2004/0081340 A1 * | 4/2004 | Hashimoto | A61B 8/00 382/128 |
| 2005/0049502 A1 * | 3/2005 | Schoisswohl | A61B 8/0866 600/453 |
| 2005/0251039 A1 * | 11/2005 | Chalana | A61B 5/204 600/437 |
| 2006/0058650 A1 * | 3/2006 | Sharony | A61B 8/0866 600/437 |
| 2007/0167760 A1 | 7/2007 | Kim et al. | |
| 2007/0255138 A1 | 11/2007 | Kristofferson et al. | |
| 2013/0335441 A1 * | 12/2013 | Zalev | A61B 5/7203 345/629 |
| 2014/0152661 A1 * | 6/2014 | Nishiura | A61B 19/50 345/424 |
| 2014/0330121 A1 | 11/2014 | Kim | |
| 2015/0116323 A1 * | 4/2015 | Buckton | G06T 19/00 345/424 |
| 2015/0297090 A1 * | 10/2015 | Herzog | A61B 8/4254 600/437 |

* cited by examiner

```
For every (x , y) pixel in the output image
    float4 f4Color=0 ;

float intensity = inputVolume ((x, y, z));

float4 f4Sample = transfer (intensity, t, x, y) ;
        // rgb=color, a=alpha
    float3 f3Gradient = gradient (inputVolume
    (x, y, z)) ;   // computed with e.g. central
    differences, points in direction of strongest change
        float fBrightness = f3LightColor * max (0 , dot
    (normalize (f3Gradient) , f3LightDirection)) ; // very
    simple diffuse shading
        f4Ccolor += (1 - f4Color.a) *
    f4Sample*f3Brightness;
    end
end
```

METHOD AND APPARATUS FOR RENDERING AN ULTRASOUND IMAGE

BACKGROUND

Technical Field

Embodiments of the invention relate generally to rendering ultrasound images. Particular embodiments relate to fetal ultrasound imaging.

Discussion of Art

Ultrasound medical imaging is typically used to survey internal structures for diagnostic purposes. Ultrasound has several unique features including comparatively short image acquisition times, on the order of one half second compared to several seconds for MRI, the ability to acquire many images with minimal patient risk, and an interactive role for a technician as part of the imaging system control loop. As a result, ultrasound is particularly useful for imaging moving internal structures, e.g., for fetal imaging during gestation.

With reference to fetal imaging, ultrasound serves more than merely diagnostic purposes. The presentation of a live image to prospective parents can promote emotional bonding of parents to their offspring, and enhance motivation to comply with well-baby practices recommended by obstetric professionals. Moreover, it is pleasing for prospective parents to feel that they are seeing how things appear within the womb. As will be appreciated, womb and fetal images, and, indeed, all ultrasound images that display a high degree of realism are desirable.

In fetal ultrasound, amniotic fluid has conventionally been treated as a completely transparent medium that does not affect light or produce any scattering or refraction effects. This treatment has been achieved by setting the opacity function, for scalar values below the threshold of amniotic fluid, to zero. As a result, amniotic fluid is not accounted for during image rendering. Failure to account for amniotic fluid, however, could potentially result in images that are less than realistic. For example, amniotic fluid scatters "light" (ultrasound) around the fetus. Also, the chemical composition of amniotic fluid, mainly lipids, causes strong specular highlights on fetal skin.

In view of the above, it is desirable to provide apparatus and methods for enhancing the realism of a fetal image, and, in particular, for representing amniotic fluid in an ultrasound image.

BRIEF DESCRIPTION

In an embodiment of the invention, a method for rendering an image from ultrasound image data includes dividing the ultrasound image data into at least a first group of voxels and a second group of voxels, based on comparing voxel echo intensity to a threshold value. The method further includes processing the first group of voxels according to a first protocol and processing the second group of pixels according to a second protocol. The method further includes generating an image that includes both the first group of processed voxels and the second group of processed voxels to enhance realism of the rendered image.

In other embodiments, a method for visualizing amniotic fluid via ultrasound imaging includes obtaining ultrasound image data, the data containing multiple voxels, and identifying tissue voxels and amniotic fluid voxels from the multiple voxels. The method further includes assigning a non-zero value to an attenuation coefficient of the amniotic fluid voxels and generating an ultrasound image that includes the amniotic fluid as well as tissue.

Yet other embodiments of the invention provide an apparatus for rendering an image from ultrasound image data. The apparatus includes a display-processing unit, which is operatively connected to obtain the ultrasound image data from an ultrasound probe, and is configured to implement a process that includes dividing the ultrasound image data into at least a first group of voxels and a second group of voxels, based on comparing voxel echo intensity to a threshold value, processing the first group of voxels according to a first protocol, processing the second group of voxels according to a second protocol, and generating an image that includes the first group of processed voxels and the second group of processed voxels to enhance realism of the rendered image.

DRAWINGS

The present invention will be better understood from reading the following description of non-limiting embodiments, with reference to the attached drawings, wherein below:

FIG. 5 shows pseudocode for raytracing voxels to provide an image according to an embodiment of the invention.

DETAILED DESCRIPTION

Figure 1:
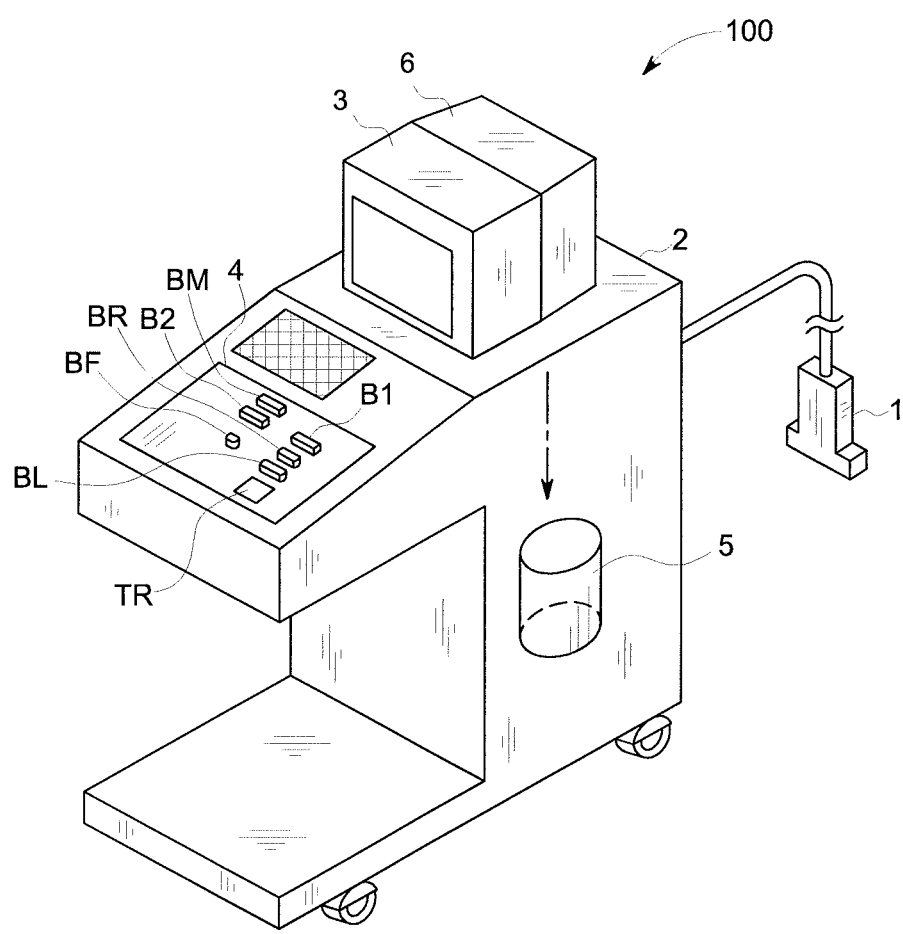
FIG. 1 is a perspective view schematically showing an ultrasound diagnostic apparatus configured for implementing an embodiment of the present invention.

Reference will be made below in detail to exemplary embodiments of the invention, examples of which are illustrated in the accompanying drawings. Wherever possible, the same reference characters used throughout the drawings refer to the same or like parts, without duplicative description. Although exemplary embodiments of the present invention are described with respect to fetal imaging, fetal tissue and amniotic fluid, embodiments of the invention are also useful for representing participating media in ultrasound images generally. In particular, embodiments of the present invention may be used to render images that include both tissue, e.g., skin, muscle, fat, organs, and non-tissue materials such as bone, water and the like. As will be appreciated, the present invention is not limited to rendering human tissue and embodiments may be used in both veterinary and human applications where appropriate.

As used herein, the terms "substantially," "generally," and "about" indicate conditions within reasonably achievable manufacturing and assembly tolerances, relative to ideal desired conditions suitable for achieving the functional purpose of a component or assembly.

By way of background, embodiments of the present invention may be utilized with ultrasound diagnostic apparatus such as the apparatus 100 depicted in FIG. 1. As shown, the apparatus 100 includes an ultrasonic probe 1 which transmits an ultrasonic pulse into a subject, e.g., the body of a human patient, and receives an ultrasonic echo from within the subject. The apparatus 100 further includes an ultrasound diagnostic apparatus body 2, which generates an ultrasound image on the basis of the ultrasonic echo, and a monitor 3 that displays the ultrasound image. The ultrasound diagnostic apparatus body 2 is provided with an operation panel 4, which accepts the operator's instructions, and a storage device 5, e.g., a hard drive, for storing ultrasound images and values of each item measured from the images. As shown, the operator's panel includes conventional ultrasound imaging controls including, for example, an image list button BM, a record button B1, an image pickup condition recall button B2, a display zoom button BR, a freeze button BF, a position record button BL, and a cursor track ball TR.

The apparatus 100 further includes a display-processing unit 6. An example of actual hardware of the display-processing unit 6 may include a central processing unit which performs processing, ROM, in which a program of the above-described configuration is stored dedicated to reading, and RAM which can be used as a working area and may rewritably store various data. All hardware components may be interconnected via a bus.

In use, the ultrasonic probe 1 emits one or more ultrasonic pulses scheduled at a pulse repetition frequency and recovers ultrasonic echo signals that are returned from the subject to a plurality of two-dimensionally distributed sampling points. The probe 1 transmits ultrasound pulse sequences and receives echo signals according to conventional modes of operation and image pickup conditions, e.g., the type of ultrasonic probe used. The probe 1 then transduces the ultrasonic echo signals into digital data that is sent to a display-processing unit. The display-processing unit 6 then generates ultrasound images on the basis of the digital data provided from the ultrasonic probe 1 and sends the ultrasound images to the monitor or other display 3.

Figure 2:
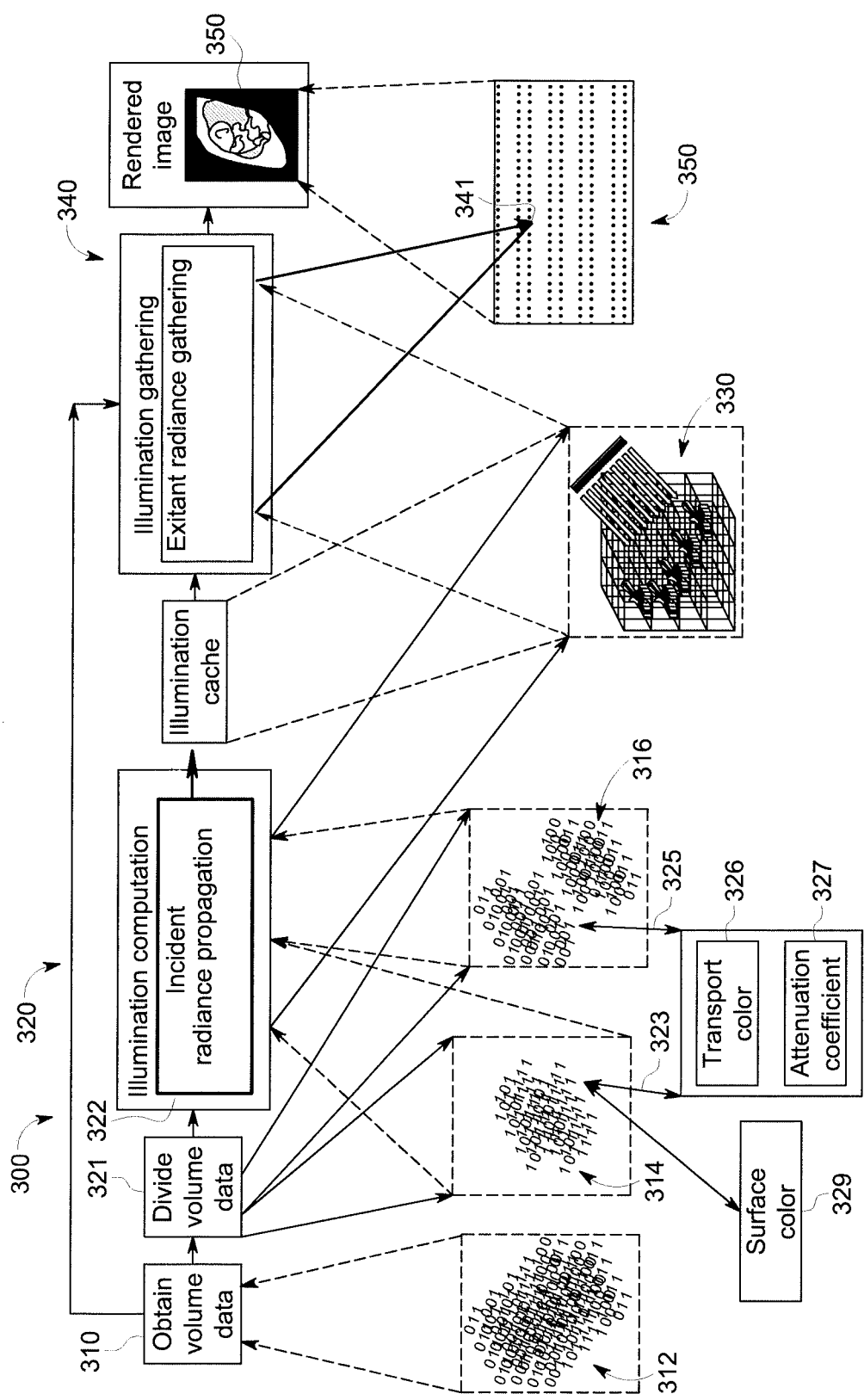
FIG. 2 is a schematic diagram showing a method for rendering amniotic fluid as a participating medium, according to an embodiment of the invention.

Turning now to FIG. 2, a method 300 for representing a non-tissue material, such as amniotic fluid, as a participating medium is depicted according to an embodiment of the invention. In the figure, dotted arrows correspond to data flow into a process or method step, whereas solid lines correspond to data flow from a process or method step. In certain embodiments, the method 300 can be implemented within an image-processing unit, particularly within the display-processing unit 6, of apparatus 100.

As shown, the method 300 includes obtaining 310 ultrasound image (volume) data 312. More specifically, in this step, the ultrasonic probe 1 is caused to transmit ultrasound pulse sequences and to receive echo series according to conventional modes of operation and image pickup conditions. Based on the ultrasound image data, the display processing unit 6 renders 340 an image 350. The image 350 may be formatted as an RGB pixel array (e.g., PNG or JPG), or as a vector graphics file (e.g., SVG), or as a mixed format (e.g., EPS). The display-processing unit 6 may render multiple images 350, e.g., from various viewing angles, and/or with varying lighting values as further discussed below.

In certain embodiments, the display processing unit 6 renders 340 the image 350 by first computing 320 incident illumination to produce an illumination cache 330. The unit 6 then gathers illumination data from the illumination cache 330 in order to render 340 the image 350. Computing 320 the incident illumination, however, is not an essential aspect of the invention. For example, according to embodiments of the invention the display-processing unit 6 may simply implement direct volume rendering of the ultrasound image data. Alternatively, beyond the computations discussed with reference to FIG. 2, the display processing unit 6 may additionally make use of multiple light sources, may use surface and volume phase functions to simulate scattering of light within the imaged volume, and/or may calculate refractions of render rays at boundaries between different materials.

Continuing to refer to FIG. 2, the step of computing 320 illumination includes calculation of incident radiance propagation 322. The illumination computation 320 produces the illumination cache 330, which then is passed into a computation of illumination gathering 340. The illumination gathering computation step 340 renders an image 350. As discussed in greater detail herein, the non-tissue material, e.g., amniotic fluid, is considered as a participating medium.

According to certain embodiments, in order to populate the illumination cache 330, the image display-processing unit 6 computes 320 incident radiance propagation 322 from each light source to each voxel of the ultrasound image (volume) data 312. In embodiments, the incident radiance propagation 322 is achieved by ray casting from each light source along its respective light propagation direction(s). At each voxel along each cast ray, the light is attenuated, i.e., part of the light is absorbed within each voxel. The exact amount of absorbed light depends on an attenuation coefficient 327 as well as a transport color 326 of the voxel. The transport color 326 is a chromatic function that depends on a scalar echo intensity value at a present voxel. The attenuation coefficient 327 is scalar amplitude multiplied by the transport color 326. Generally, higher scalar echo intensity values lead to higher attenuation coefficient amplitudes, so that such voxels absorb more light across all wavelengths.

Amniotic fluid and other non-tissue materials have traditionally been thresholded out of the incident radiance computations 320 by setting transport color 326 and attenuation coefficient 327 to null or zero values for all voxels that have scalar echo intensities less than about 0.2. However, an aspect of the invention is to not exclude non-tissue materials such as amniotic fluid amniotic fluid from the computations 320.

More specifically, embodiments of the invention differentiate the ultrasound image data 312 as a function of tissue intensity. For example, the data 312 can be divided into voxels that represent tissue, e.g., fetal tissue, and voxels that represent amniotic fluid, or other non-tissue material, for separate processing and inclusion in the final rendered ultrasound image.

As shown in FIG. 2, the image data 312 is divided at step 321 into a first group of voxels 314 that are identified as tissue, or into a second group of voxels 316 that are identified as amniotic fluid or other non-tissue material. In certain embodiments, the division of voxels is made by comparing voxel echo intensity to a threshold value. For example, in a specific embodiment, voxels that have a scalar echo intensity of >=about 0.2, i.e., the threshold value, are considered fetal tissue and those that have a scalar echo intensity <about 0.2 are considered to be amniotic fluid. While the threshold value may be set to about 0.2, in certain embodiments the value may be greater or lower that 0.2.

While exemplary embodiments divide voxels into two groups, in other embodiments, voxels may be divided into more than two groups. For example, voxels may be divided into three or more groups that correspond to different materials, such as tissue, bone and fluid, for later inclusion in a rendered image.

Figure 3:
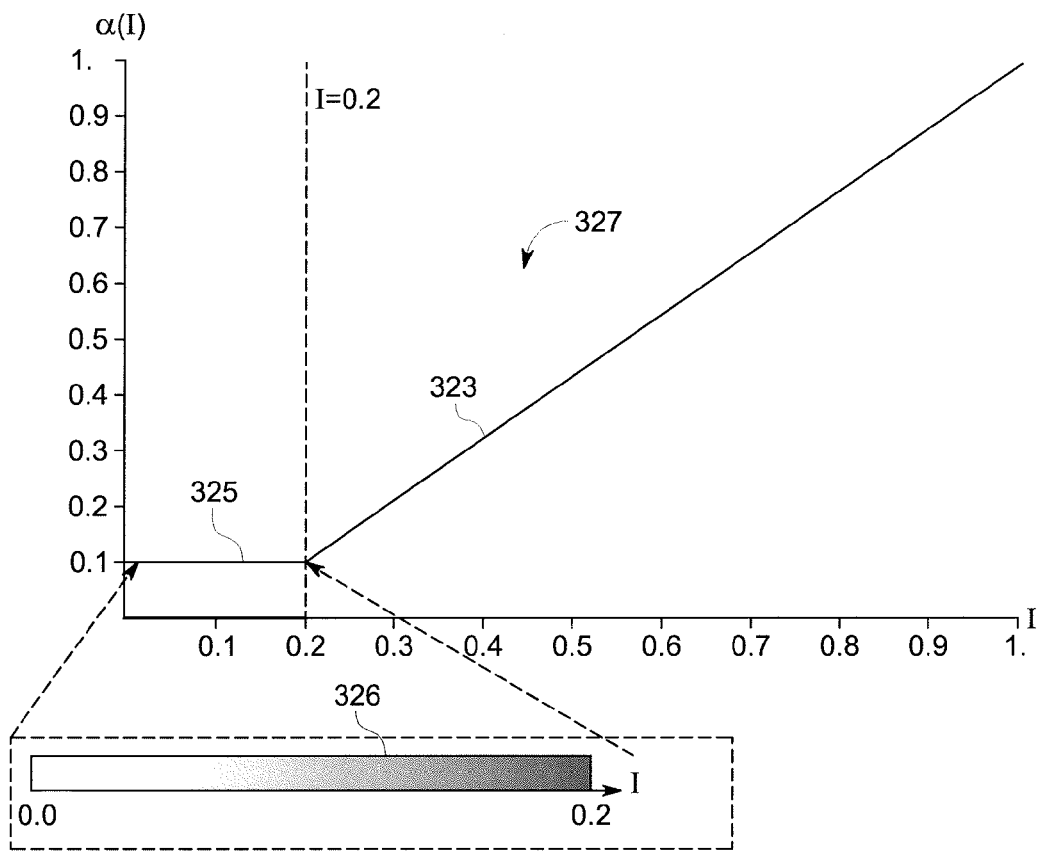
FIG. 3 is a graph comparing opacity function $\alpha(I)$, according to an embodiment of the invention, to a conventional opacity function.

Referring now to FIG. 3, after the voxels are divided into first and second groups at step 321, the groups are processed differently. In an embodiment, the respective groups of voxels are processed according to first and second protocols. Each protocols assigns its respective group at least one optical properties. In context of this disclosure, an "optical property" refers to a material property that affects the propagation of human-visible light, i.e., light having a wavelength between about 400 nm and about 700 nm. Exemplary optical properties include opacity (attenuation coefficient), transport color, surface color, refractive index, surface phase function, and the like.

The optical properties may be assigned based on voxel echo intensity values and/or voxel position. For at least one of the optical properties, values of that optical property are assigned to voxels 314 of the first group according to a different function than is used for assigning values of that optical property to voxels 316 of the second group.

As used herein, "function" refers to a relation between a set of inputs and a set of outputs with the property that each input is related to exactly one permissible output. For example, a function could have a scalar input (e.g., an ultrasound echo intensity value) or it could have a vector input (e.g., an ultrasound voxel location). Similarly, a function could have a scalar output (e.g., an attenuation coefficient) or it could have a vector output (e.g., a transport color function expressed as a vector in color space). In any case, for any possible input value, the function would have only one corresponding output value.

For example, in the embodiment of the invention shown in FIG. 3, the respective groups of voxels may be processed according to first and second protocols 323, 325. Under a first protocol 323, voxels 314 of the first group, which represent fetal tissue, are assigned a constant value for transport color 326 and are assigned values of the attenuation coefficient 327 as a linear function of scalar echo intensity value. For the second group of voxels 316, which represent amniotic fluid, a second protocol 325 assigns transport color 326 as a function of scalar echo intensity value, and assigns attenuation coefficient 327 as a non-zero value, which, in an embodiment, may be a constant.

More specifically, according to the first protocol 323, the opacity (attenuation coefficient 327) of tissue voxels, i.e., the first group of voxels 314, is set to a linear function of scalar echo intensity. In contrast, according to the second protocol 325, opacity (attenuation coefficient 327) of amniotic fluid voxels 316 is set to a non-zero flat attenuation constant, i.e., light of any wavelength slightly attenuates while it passes through the amniotic fluid. In other embodiments, however, the first protocol 323 may impose a uniformly high value (e.g., 0.9) for the attenuation coefficient 327 of all of the first group of (tissue) voxels 314, while the second protocol 325 may assign values to the attenuation coefficient 327 of the second group of (amniotic fluid) voxels 316, according to any non-zero function of voxel echo intensity, e.g., a step function, a ramp function, a power function, an exponential function.

Additionally, the second protocol 325 may set the transport color function 326 for the second group of amniotic fluid voxels 316 to approximate measured optical properties of water. This approximation for the second group of voxels 316 can yield a transport color function 326 that varies from transparent through light blue hues, according to increasing values of scalar echo intensity. Generally, practically measured water phase functions, based on Rayleigh scattering, can be used as a starting point for treatment of amniotic fluid as a participating medium. As will be appreciated, in certain embodiments, it may be possible to use fluid approximations other than water.

Continuing to refer to FIG. 2, each voxel 314 or 316 is characterized by its transport color 326 and by its attenuation coefficient 327. According to embodiments, each of the first group of voxels 314 also can be described by a diffuse surface color 329. The diffuse surface color 329 can be made dependent on angle (and distribution) between incoming light and outgoing direction, utilizing a phase function to further enhance the physical lighting mode.

Figure 4:
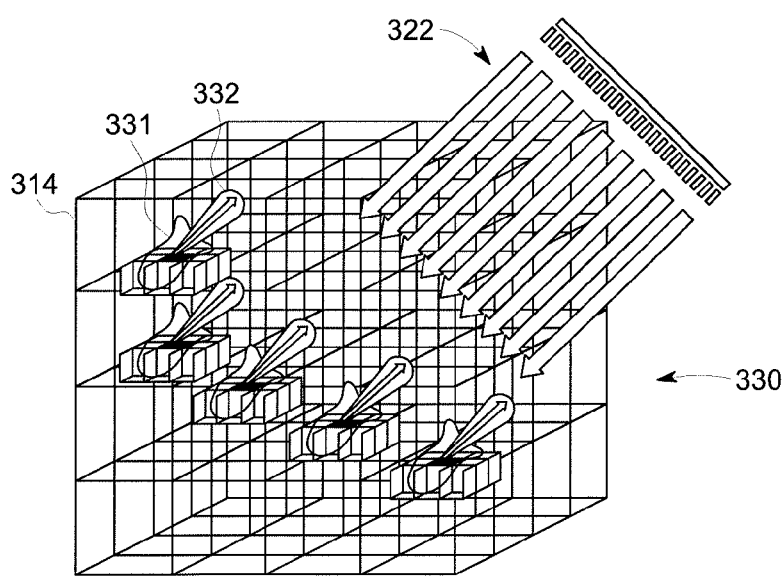
FIG. 4 is a schematic showing an illumination cache produced at an incident radiance propagation step of the method shown in FIG. 2.

Referring also now to FIG. 4, while computing incident radiance propagation 322, the image display-processing unit 106 stores the resulting voxel-by-voxel values of color intensity 331 (per R, G and B channel) and directional components 332 within the illumination cache 330. Moreover, hard shadows are formed at this stage in the illumination cache 330. The data stored within the illumination cache 330 is graphically illustrated at FIG. 4.

Referring back to FIG. 2, at the stage of illumination gathering computation 340, the display processing unit 6 accumulates at each display pixel 341 color and opacity values from the incident radiances obtained from the illumination cache 330 for each voxel 314 or 316 focused at the display pixel 341. For example, FIG. 5 shows pseudocode for an embodiment of the illumination gathering computation 340.

Accordingly, embodiments of the invention implement a method for rendering an image from ultrasound image data includes dividing the ultrasound image data into at least a first group of voxels and a second group of voxels, based on comparing voxel echo intensity to a threshold value. The method further includes processing the first group of voxels according to a first protocol and processing the second group of voxels according to a second protocol. Additionally, the method includes generating an image that includes the first group of processed voxels and the second group of processed voxels to enhance realism of the rendered image. In embodiments, the threshold value is selected such that the first group of voxels have echo intensity values associated with tissue and the second group of voxels have echo intensity values associated with a non-tissue material. Non-tissue material includes bone, blood vessels, and/or fluids. In certain embodiments, the threshold value is selected such that the first group of voxels have echo intensity values associated with fetal tissue and the second group of voxels have echo intensity values associated with amniotic fluid. In an embodiment, the first protocol sets values of at least one optical property according to a first function and the second protocol sets values of the at least one optical property according to a second function, the second function being different from the first function. The at least one optical property includes one of opacity, surface color, transport color, phase function, or refraction coefficient. In embodiments, each voxel is divided into the first group if it has an echo intensity of greater than or equal to about 0.2 and voxel is divided into the second group if it has an echo intensity of less than about 0.2. The second protocol may include assigning transport color as a function of echo intensity, which may approximate the wavelength function of water. The first protocol and the second protocol may further include propagating and attenuating incident radiance which may be accomplished via ray casting from at least one light source. In an embodiment, under the second protocol the attenuation coefficient is considered as a non-zero value that is no larger than a least value assigned to the attenuation coefficient according to the first protocol.

In other embodiments, a method for visualizing amniotic fluid via ultrasound imaging includes obtaining ultrasound image data, the data containing multiple voxels and identifying tissue voxels and amniotic fluid voxels from the multiple voxels. The method further includes assigning a non-zero value to an attenuation coefficient of the amniotic fluid voxels and generating an ultrasound image that includes the amniotic fluid as well as tissue. In embodiments, the step of identifying tissue voxels and amniotic fluid voxels includes comparing an echo intensity of the multiple voxels to a threshold value, which may be about 0.2. The method may further include assigning transport color to the amniotic fluid voxels as a function of echo intensity, the transport color may be set to approximate the wavelength function of water.

Yet other embodiments of the invention provide an apparatus for rendering an image from ultrasound image data. The apparatus includes a display-processing unit, which is operatively connected to obtain the ultrasound image data from an ultrasound probe, and is configured to implement a process includes dividing the ultrasound image data into at least a first group of voxels and a second group of voxels, based on comparing voxel echo intensity to a threshold value, processing the first group of voxels according to a first protocol, processing the second group of voxels according to a second protocol, and generating an image that includes the first group of processed voxels and the second group of processed voxels to enhance realism of the rendered image. In an embodiment, the threshold value is selected such that the first group of voxels have echo intensity values associated with tissue and the second group of voxels have echo intensity values associated with a non-tissue material.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice embodiments of the invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal language of the claims.

As used herein, an element or step recited in the singular and proceeded with the word "a" or "an" should be understood as not excluding plural of the elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. A method for rendering an image from ultrasound image data, comprising:
    dividing the ultrasound image data into at least a first group of voxels and a second group of voxels, based on comparing voxel echo intensity to a threshold value;
    processing the first group of voxels according to a first protocol;
    processing the second group of voxels according to a second protocol;
    generating an image that includes the first group of processed voxels and the second group of processed voxels to enhance realism of the rendered image; and
    wherein the second protocol includes assigning transport color as a function of echo intensity, and
    the second protocol assigns the transport color to approximate a wavelength function of water.

2. The method of claim 1, wherein the first protocol and the second protocol further comprise:
    propagating and attenuating incident radiance.

3. The method of claim 2, wherein the propagating and attenuating are accomplished via ray casting from at least one light source.

4. The method of claim 1, wherein the threshold value is selected such that the first group of voxels have echo intensity values associated with tissue and the second group of voxels have echo intensity values associated with a non-tissue material.

5. The method of claim 4, wherein the non-tissue material includes bone and/or fluids.

6. The method of claim 1, wherein the threshold value is selected such that the first group of voxels have echo intensity values associated with fetal tissue and the second group of voxels have echo intensity values associated with amniotic fluid.

7. The method of claim 1, wherein the first protocol sets values of at least one optical property according to a first function and the second protocol sets values of the at least one optical property according to a second function, the second function being different from the first function.

8. The method of claim 7, wherein the at least one optical property includes one of opacity, surface color, phase function, or refraction coefficient.

9. The method of claim 1, wherein each voxel is divided into the first group if it has an echo intensity of greater than or equal to about 0.2.

10. The method of claim 1, wherein each voxel is divided into the second group if it has an echo intensity of less than about 0.2.

11. A method for rendering an image from ultrasound image data, comprising:
- dividing the ultrasound image data into at least a first group of voxels and a second group of voxels, based on comparing voxel echo intensity to a threshold value;
- processing the first group of voxels according to a first protocol;
- processing the second group of voxels according to a second protocol;
- generating an image that includes the first group of processed voxels and the second group of processed voxels to enhance realism of the rendered image;
- wherein the first protocol and the second protocol further comprise: propagating and attenuating incident radiance; and
- wherein under the second protocol the attenuation coefficient is considered as a non-zero value that is no larger than a least value assigned to the attenuation coefficient according to the first protocol.

12. The method of claim 11, wherein the threshold value is selected such that the first group of voxels have echo intensity values associated with tissue and the second group of voxels have echo intensity values associated with a non-tissue material.

13. The method of claim 12, wherein the non-tissue material includes bone and/or fluids.

14. The method of claim 11, wherein the threshold value is selected such that the first group of voxels have echo intensity values associated with fetal tissue and the second group of voxels have echo intensity values associated with amniotic fluid.

15. The method of claim 11, wherein the first protocol sets values of at least one optical property according to a first function and the second protocol sets values of the at least one optical property according to a second function, the second function being different from the first function.

16. The method of claim 15, wherein the at least one optical property includes one of opacity, surface color, transport color, phase function, or refraction coefficient.

17. The method of claim 11, wherein each voxel is divided into the first group if it has an echo intensity of greater than or equal to about 0.2.

18. A method for visualizing amniotic fluid via ultrasound imaging comprising:
- obtaining ultrasound image data, the data containing multiple voxels;
- identifying tissue voxels and amniotic fluid voxels from the multiple voxels, wherein the step of identifying tissue voxels and amniotic fluid voxels includes comparing an echo intensity of the multiple voxels to a threshold value;
- assigning a non-zero value to an attenuation coefficient of the amniotic fluid voxels;
- generating an ultrasound image that includes the amniotic fluid as well as tissue; and
- assigning transport color to the amniotic fluid voxels as a function of echo intensity.

19. The method of claim 18, wherein the transport color is set to approximate a wavelength function of water.

20. The method of claim 18, wherein the threshold value is about 0.2.

* * * * *